(12) United States Patent
Nason et al.

(10) Patent No.: US 12,390,596 B2
(45) Date of Patent: Aug. 19, 2025

(54) SYRINGES CONFIGURED TO INHIBIT FORWARD PLUNGER MOVEMENT

(71) Applicant: Kurin, Inc., San Diego, CA (US)

(72) Inventors: Kevin Nason, Phoenix, AZ (US);
Jeffrey Veloz, San Diego, CA (US);
Bobby E. Rogers, Park City, UT (US);
Nolan Pupping, Carlsbad, CA (US)

(73) Assignee: Kurin, Inc., San Diego, CA (US)

( * ) Notice: Subject to any disclaimer, the term of this patent is extended or adjusted under 35 U.S.C. 154(b) by 0 days.

(21) Appl. No.: 18/595,845

(22) Filed: Mar. 5, 2024

(65) Prior Publication Data

US 2024/0198005 A1    Jun. 20, 2024

Related U.S. Application Data

(63) Continuation of application No. 18/083,359, filed on Dec. 16, 2022.

(60) Provisional application No. 63/291,330, filed on Dec. 17, 2021.

(51) Int. Cl.
*A61B 5/153* (2006.01)
*A61M 5/31* (2006.01)
*A61M 5/315* (2006.01)

(52) U.S. Cl.
CPC .......... *A61M 5/3134* (2013.01); *A61B 5/153* (2013.01); *A61M 5/31501* (2013.01); *A61M 5/31595* (2013.01); *A61M 2005/3128* (2013.01); *A61M 2005/31508* (2013.01)

(58) Field of Classification Search
CPC ............ A61M 5/3134; A61M 5/31595; A61M 5/31501; A61M 2005/3128; A61M 2005/31508; A61B 5/153

See application file for complete search history.

(56) References Cited

U.S. PATENT DOCUMENTS

| | | |
|---|---|---|
| 1,166,030 A | 12/1915 | Willower |
| 3,859,998 A | 1/1975 | Thomas |
| 3,886,930 A | 6/1975 | Ryan |
| 4,207,870 A | 6/1980 | Eldridge |
| 4,370,987 A * | 2/1983 | Bazell .............. A61B 5/150526 600/573 |
| 4,373,535 A | 2/1983 | Martell |
| 4,690,154 A | 9/1987 | Woodford |

(Continued)

FOREIGN PATENT DOCUMENTS

WO     2012012127    1/2012

OTHER PUBLICATIONS

International Search Report and Written Opinion mailed May 4, 2023, International Application No. PCT/IB2022/062419; (23 pages).

(Continued)

*Primary Examiner* — Tasnim Mehjabin Ahmed
(74) *Attorney, Agent, or Firm* — Pillsbury Winthrop Shaw Pittman LLP

(57) ABSTRACT

Disclosed are systems that include a syringe having a barrel configured to hold a fluid and a plunger configured to draw the fluid into the barrel when the plunger is pulled backward through the barrel. The syringe is configured to inhibit forward movement of the plunger. For example, the systems can include mating pockets configured to engage barbs to inhibit forward movement of the plunger.

48 Claims, 23 Drawing Sheets

(56) References Cited

U.S. PATENT DOCUMENTS

| | | | |
|---|---|---|---|
| 4,995,869 A * | 2/1991 | McCarthy | A61M 5/5013 604/110 |
| 5,037,393 A * | 8/1991 | Ellgass | A61M 5/348 604/218 |
| 5,084,017 A | 1/1992 | Maffetone | |
| 5,097,842 A | 3/1992 | Bonn | |
| 5,174,301 A | 12/1992 | Sarstedt | |
| 5,865,803 A | 2/1999 | Major | |
| 5,873,841 A | 2/1999 | Brannon | |
| 6,013,037 A * | 1/2000 | Brannon | A61B 5/150496 600/576 |
| 6,913,580 B2 | 7/2005 | Stone | |
| 8,535,241 B2 | 9/2013 | Bullington | |
| 10,265,007 B2 | 4/2019 | Bullington | |
| 10,299,713 B2 | 5/2019 | Patton | |
| 10,596,615 B2 | 3/2020 | Cavicchia | |
| 10,624,977 B2 | 4/2020 | Bullington | |
| 10,881,343 B2 | 1/2021 | Bullington | |
| 11,213,232 B2 | 1/2022 | Ivosevic | |
| 11,234,626 B2 | 2/2022 | Bullington | |
| 11,259,727 B2 | 3/2022 | Bullington | |
| 11,395,612 B2 | 7/2022 | Bullington | |
| 11,419,531 B2 | 8/2022 | Bullington | |
| 11,439,332 B2 | 9/2022 | Bullington | |
| 11,589,843 B2 | 2/2023 | Bullington | |
| 11,612,340 B2 | 3/2023 | Bullington | |
| 11,653,863 B2 | 5/2023 | Bullington | |
| 11,737,693 B2 | 8/2023 | Bullington | |
| 11,786,155 B2 | 10/2023 | Bullington | |
| 11,789,017 B2 | 10/2023 | Bullington | |
| 2005/0273019 A1 | 12/2005 | Conway | |
| 2008/0167577 A1 | 7/2008 | Weilbacher | |
| 2015/0073348 A1 | 3/2015 | Bullington | |
| 2015/0105754 A1 * | 4/2015 | Roche | A61M 1/815 604/542 |
| 2015/0351678 A1 | 12/2015 | Bullington | |
| 2018/0140240 A1 | 5/2018 | Bullington | |
| 2020/0289039 A1 | 9/2020 | Bullington | |
| 2021/0275068 A1 | 9/2021 | Miazga | |
| 2022/0151525 A1 | 5/2022 | Bullington | |
| 2022/0151527 A1 | 5/2022 | Bullington | |
| 2022/0160271 A1 | 5/2022 | Ivosevic | |
| 2022/0304600 A1 | 9/2022 | Hammer | |
| 2022/0304664 A1 | 9/2022 | Hammer | |
| 2023/0191033 A1 * | 6/2023 | Nason | A61M 5/31595 604/187 |

OTHER PUBLICATIONS

Zimmon, David S. et al. "Effect of portal venous blood flow diversion on portal pressure." The Journal of Clinical Investigation 65.6 (1980): 1388-1397.

Patton, Richard G., et al. "Innovation for reducing blood culture contamination: initial specimen diversion technique." Journal of clinical microbiology 48.12 (2010): 4501-4503.

Tang, Menglin, et al. "Closed blood conservation device for reducing catheter-related infections in children after cardiac surgery." Critical Care Nurse 34.5 (2014): 53-60.

Ernst, Dennis J. et al. "NCCLS simplifies the order of draw: a brief history." MLO: medical laboratory observer 36.5 (2004): 1-5 pages.

Gottlieb, T. "Hazards of bacterial contamination of blood products." Anaesthesia and intensive care 21.1 (1993): 20-23.

Norberg, Alonna, et al. "Contamination rates of blood cultures obtained by dedicated phlebotomy vs intravenous catheter." Jama 289.6 (2003): 726-729.

Quilici, Nathalie, et al. "Differential quantitative blood cultures in the diagnosis of catheter-related sepsis in intensive care units." Clinical infectious diseases 25.5 (1997): 1066-1070.

Napolitano, Marcello, et al. "Quality control of bacterial contamination of blood components: the feasibility of diversion system testing." Blood Transfus 2 (2004): 231-232.

De Korte, Dirk, et al. "Effects of skin disinfection method, deviation bag, and bacterial screening on clinical safety of platelet transfusions in the Netherlands." Transfusion 46.3 (2006): 476-485.

Liumbruno, Giancarlo Maria, et al. "Reduction of the risk of bacterial contamination of blood components through diversion of the first part of the donation of blood and blood components." Blood Transfusion 7.2 (2009): 86.

NCCLS. Procedures for the Collection of Diagnostic Blood Specimens by Venipuncture; Approved Standard—Fifth Edition. H3-A5, vol. 23, No. 32. Replaces H3-A4; vol. 18, No. 7. 1-52 pages. http://demo.nextlab.ir/Organization/Documents/CLSI-Standards/CLSI-H3-A5.aspx.

Challiner, A., et al. "Venous/arterial blood management protection system." Anaesthesia 47.2 (1992): 169-169.

Murphy, Michael F. "Better Blood Transfusion." Journal of the Intensive Care Society 4.3 (2003): 78-80.

Palavecino, Elizabeth L., et al. "Detecting bacterial contamination in platelet products." Clinical laboratory 52.9-10 (2006): 443-456.

Sheppard, Chelsea A., et al. "Bacterial contamination of platelets for transfusion: recent advances and issues." Laboratory Medicine 36.12 (2005): 767-770.

Shulman, Gerald. "Quality of processed blood for autotransfusion." Journal of Extracorporeal Technology 32.1 (2000): 11-19.

Weinbaum, Fredric I., et al. "Doing it right the first time: quality improvement and the contaminant blood culture." Journal of Clinical Microbiology 35.3 (1997): 563-565.

Weinstein, Melvin P. "Blood culture contamination: persisting problems and partial progress." Journal of clinical microbiology 41.6 (2003): 2275-2278.

Weinstein, Melvin P., et al. "The clinical significance of positive blood cultures in the 1990s: a prospective comprehensive evaluation of the microbiology, epidemiology, and outcome of bacteremia and fungemia in adults." Clinical Infectious Diseases 24.4 (1997): 584-602.

Weinstein, Melvin P. "Current blood culture methods and systems: clinical concepts, technology, and interpretation of results." Clinical infectious diseases 23.1 (1996): 40-46.

Closed IV, BD Saf-T-Intima. "Catheter System, Becton, Dickinson and Company, Brochure." Retrieved from the Internet (Aug. 23, 2019). 4 pages.

Perez, P., et al. "Multivariate analysis of determinants of bacterial contamination of whole-blood donations." Vox Sanguinis 82.2 (2002): 55-60.

McDonald, Carl P. "Interventions implemented to reduce the risk of transmission of bacteria by transfusion in the English National Blood Service." Transfusion Medicine and Hemotherapy 38.4 (2011): 255-258.

Lifesciences, Edwards. "Conservation. Safety. Simplicity. Edwards Vamp and Vamp Jr. Systems." (2002). 4 pages.

De Korte, Dirk, et al. "Diversion of first blood volume results in a reduction of bacterial contamination for whole-blood collections." Vox sanguinis 83.1 (2002): 13-16.

Brecher, Mark E., et al. "Bacterial contamination of blood components." Clinical microbiology reviews 18.1 (2005): 195-204.

Van Zundert, Adrien. "New closed IV catheter system." Acta Anæsthesiologica Belgica 56.3 (2005): 283-285.

Hall, Keri K., et al. "Updated review of blood culture contamination." Clinical microbiology reviews 19.4 (2006): 788-802.

Li, Yiwen, et al. "Direct labeling and visualization of blood vessels with lipophilic carbocyanine dye DiI." Nature protocols 3.11 (2008): 1703-1708.

Page, Catherine, et al. "Blood conservation devices in critical care: a narrative review." Annals of intensive care 3 (2013): 1-6.

Abbott Point of Care, Cartridge and Test Information, Art: 714258-010; Rev. Date: Aug. 15, 2016, 1-6 pages.

Sheppard, et al., Bacterial Contamination of Platelets for Transfusion: Recent Advances and Issues, Labmedicine, vol. 36, No. 12, Dec. 2005 ("Sheppard 2005").

*Retractable Techs., Inc. v. Becton Dickinson & Co.*, CA No. 2:07-CV-250, Claim Construction Order (E.D. Tex., Jan. 20, 2009). 20 pages.

(56) References Cited

OTHER PUBLICATIONS

Hillyer, Christopher D., et al. "Bacterial Contamination of Blood Components: Risks, Strategies and Regulation," Hematology, 2003, pp. 575-589.
PCT International Preliminary Examination Report mailed Jun. 27, 2024, International Application No. PCT/IB2022/062419; (14 pages).

* cited by examiner

SYRINGES CONFIGURED TO INHIBIT FORWARD PLUNGER MOVEMENT

RELATED APPLICATION(S)

This application is a continuation of and claims priority to and the benefit of U.S. patent application Ser. No. 18/083,359 filed Dec. 16, 2022, which claims priority to and the benefit of U.S. Provisional Application No. 63/291,330 filed Dec. 17, 2021, the contents of each are hereby incorporated by reference.

DESCRIPTION OF THE RELATED ART

A syringe is a device that can be used for injecting or withdrawing fluids, for example, to and from a body of a person. Syringes are frequently used in clinical settings to administer injections, infuse intravenous therapy into the bloodstream, or draw fluids such as venous blood from a patient.

SUMMARY

Disclosed are systems that include a syringe having a barrel configured to hold a fluid and a plunger configured to draw the fluid into the barrel when the plunger is pulled backward through the barrel. The syringe is configured to inhibit forward movement of the plunger. For example, the systems can include mating pockets configured to engage barbs to inhibit forward movement of the plunger. In some implementations, the mating pockets can be integrated into the barrel and the one or more barbs are integrated into the plunger and in other implementations the mating pockets can be integrated into the plunger and the barbs can be integrated into the barrel. The mating pockets can be integrated into a clip that may be configured to be removably attached at least partially around the plunger.

In some variations, the plunger can include an interface having an open-ended cylinder with a collection needle and a sampling channel through the plunger. The interface can include mating pockets configured to engage barbs to inhibit forward movement of the plunger. The interface can also include barbs configured to engage mating pockets to inhibit forward movement of the plunger.

In other variations, the plunger can include a plunger seal having one or more barbs, the one or more barbs configured to inhibit forward movement of the plunger.

In yet other variations, the system can include a clip configured to attach to the barrel and to securely attach to the plunger and inhibit forward movement of the plunger when the clip engages the barrel. The system can include an inner wedge adjacent the plunger and an outer wedge adjacent the barrel wherein the inner wedge and outer wedge are configured to provide frictional engagement of the inner wedge and the plunger in response to forward movement of the plunger.

In some variations, the system can include cam locks configured to inhibit forward movement of the plunger. The system can also have the plunger including a plunger seal and a wedge at least partially inside the plunger seal configured to inhibit forward movement of the plunger by increasing friction between the plunger seal and the barrel.

In other variations, the system can include a sampling channel from the tip of the syringe, through the plunger, to an interface having an open-ended cylinder with a collection needle, a barrel channel from the tip of the syringe into the barrel, and a check valve in communication with the barrel channel, the check valve being configured to check forward expulsion of fluids from the barrel.

In yet other variations, the system can include a sampling channel from a tip of the syringe, through the plunger, to an interface having an open-ended cylinder with a collection needle and a barrel channel extending from the sampling channel into the barrel. A check valve can be in communication with the barrel channel, the check valve configured to check forward expulsion of fluids from the barrel.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to particular implementations, it should be readily understood that such features are not intended to be limiting. The claims that follow this disclosure are intended to define the scope of the protected subject matter.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

DETAILED DESCRIPTION

Figure 1:
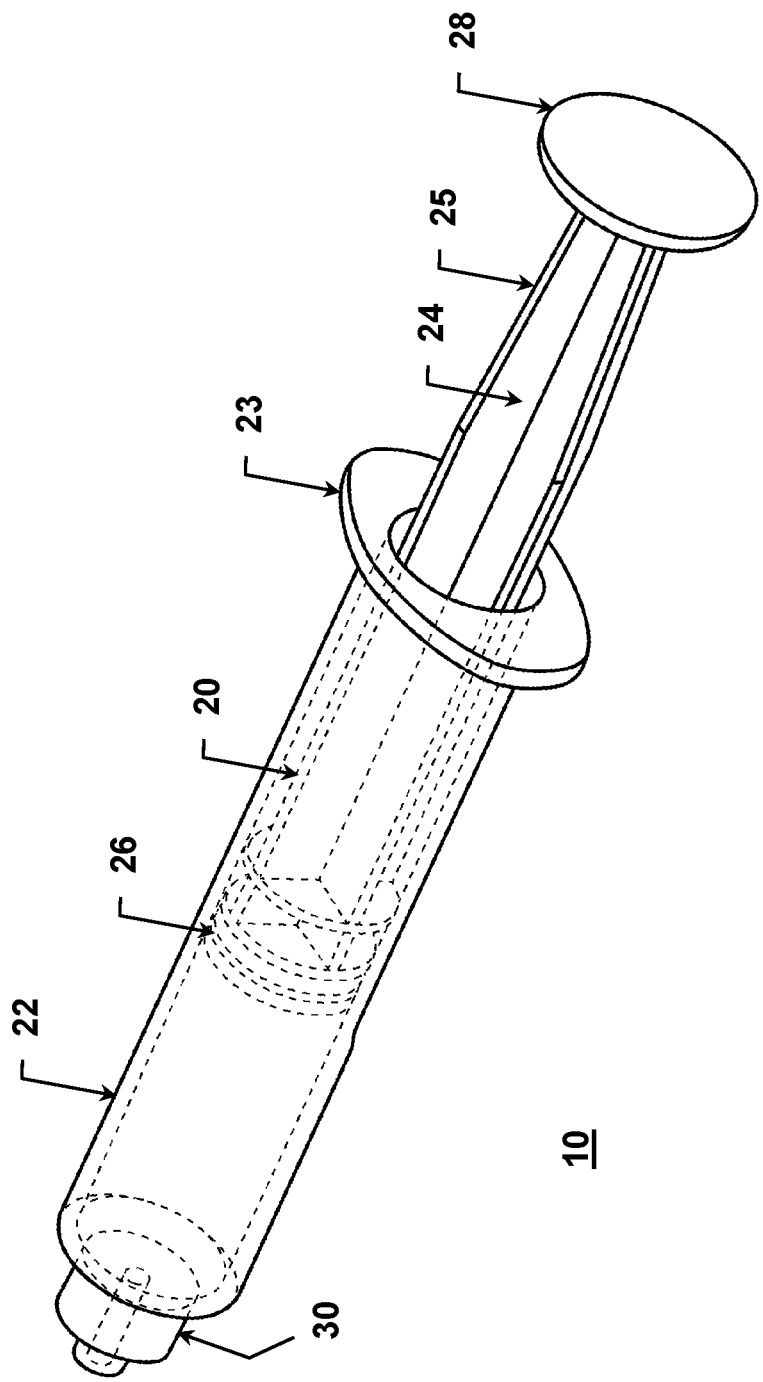
FIG. 1 illustrates an exemplary syringe in accordance with certain aspects of the present disclosure.

As illustrated in FIG. 1, exemplary syringe 10 can include a reciprocating pump, or plunger 20 that fits tightly within, but which can frictionally move along, a length of a cylindrical tube, referred to herein as a body or barrel 22. The plunger 20 can be pulled backward and/or pushed forward linearly along the inside of the barrel 22 allowing the syringe to take in or expel liquid or gas from barrel 22 through an orifice at the forward end of barrel 22 via a connection interface 30. The connection interface 30 at the forward end of the syringe can be fitted with, for example, a hypodermic needle or a threaded connector to a catheter port in order to direct the flow into and out of the barrel 22.

The barrel 22 can include a barrel flange 23 that a user can engage with one or more fingers when manipulating the syringe, for example, when pulling plunger 20 backwards (away from the patient) or when pushing plunger 20 forward (toward the patient). The barrel 22 may be marked with a number of indicia, such as lines, gradient indicators, or alphanumeric characters in order to indicate a volume or amount of fluid that can be contained with the barrel 22.

The plunger 20 can include a plunger rod 24 and a plunger piston or seal 26 at a distal end of the plunger. The plunger seal 26, or simply "seal," can be sized and configured for creating a fluid-tight seal within an inner surface or dimension of the barrel. The plunger seal 26 can be formed of a unitary piece of material, such as rubber or another pliable material, or it can include outward-extending ridges or flaps to facilitate sealing with the inner surface of barrel 22. The plunger rod 24 can include one or more longitudinal flanges 25 extending from a central part of the rod 24 and one or more latitudinal or orthogonal support flanges that extend between the longitudinal flanges. In some implementations, the plunger rod 24 can define, or include, a fluid pathway along the length of plunger 20 from the plunger seal 26 to the distal end of plunger 20.

The plunger 20 can include a plunger end 28 that may be a flat-shaped disk, or some other shape, so as to be finger-grabbable and enable a user to move plunger 20 backward and forward within the barrel 22. In some implementations, consistent with the subject matter described herein, the plunger end 28 can include a fluid collection device such as a Vacutainer™ or other type of interface that may include an open-ended cylinder with a collection needle that has a sampling channel through the length of the plunger that continues to the distal tip of the syringe (regardless of how far the plunger has been withdrawn).

Figure 6A:
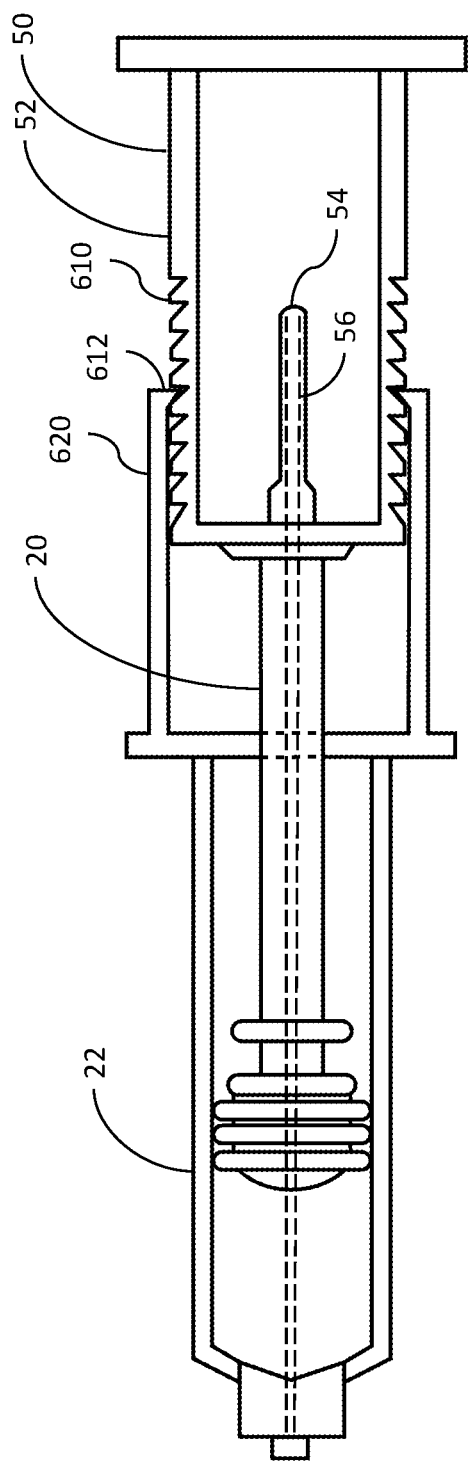
FIGS. 6A and 6B illustrate exemplary implementations of a syringe having a plunger with an open-ended cylinder interface in accordance with certain aspects of the present disclosure.

Whenever the term plunger is used herein, it contemplates various possible plunger ends such as the plunger end shown in FIG. 1 or the plunger end including an interface with an open-ended cylinder and a collection needle in FIG. 6A, a luer lock connection (male or female), etc. In addition, any plunger described herein can include a sampling channel through it (as in FIG. 6A).

The present disclosure provides syringes (or mechanisms connectible to a syringe), where the syringe has a plunger generally configured for being pulled back through a barrel to collect a fluid, but where forward movement of the plunger is inhibited. The implementations herein detail various features to inhibit forward movement in order to reduce the likelihood of expelling any portion of the collected fluid from the syringe body. Two examples for inhibiting forward movement of a plunger, described in greater detail herein, include a ratcheting mechanism within the body (e.g., using mechanical features such as barbs) and a check valve (using fluid pressure behind the check valve) to inhibit forward movement of the plunger.

Figure 2A:
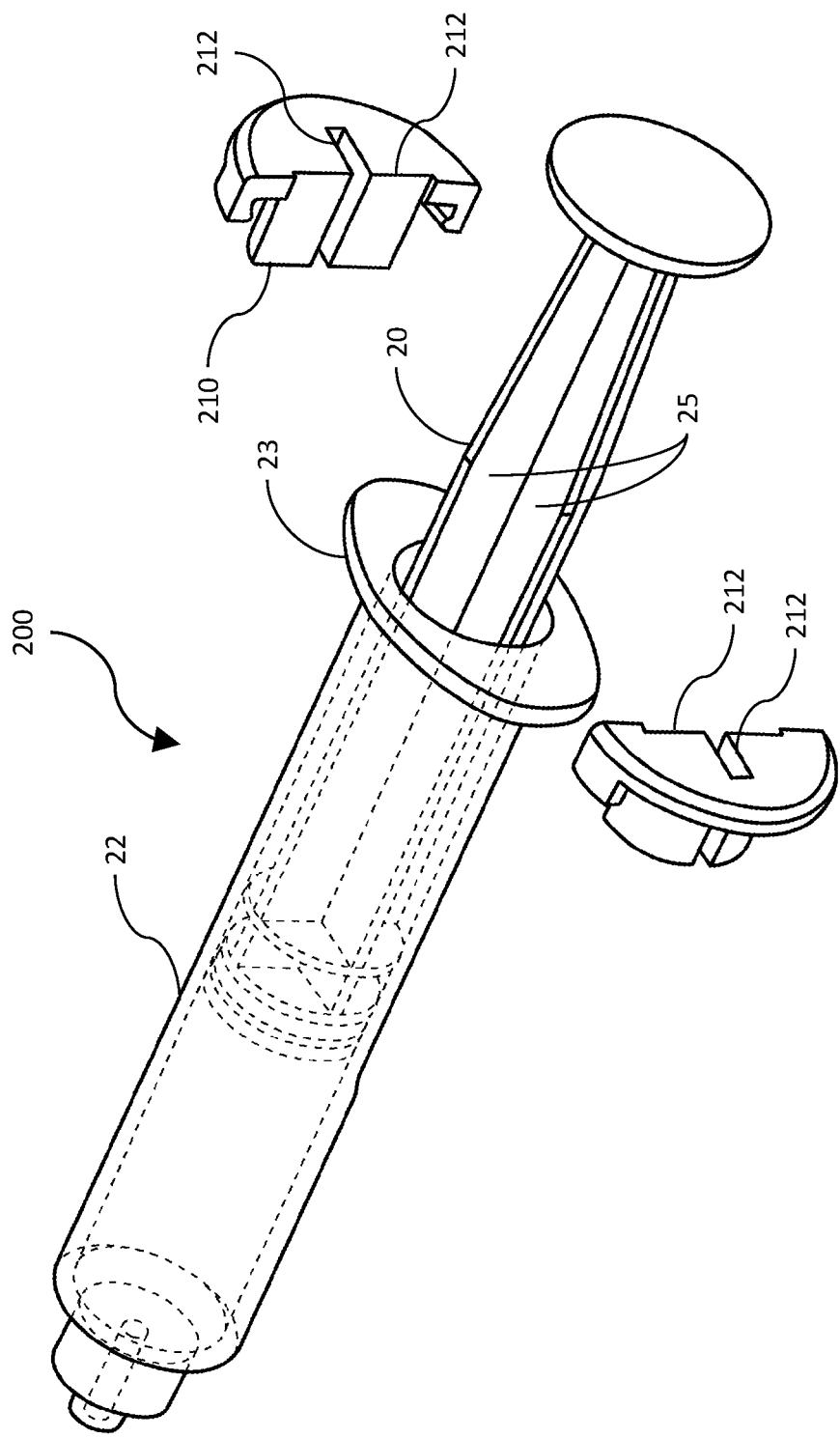
FIGS. 2A-2B illustrate an exemplary syringe with a clip that inhibits forward movement of a plunger in accordance with certain aspects of the present disclosure.
Figure 2B:
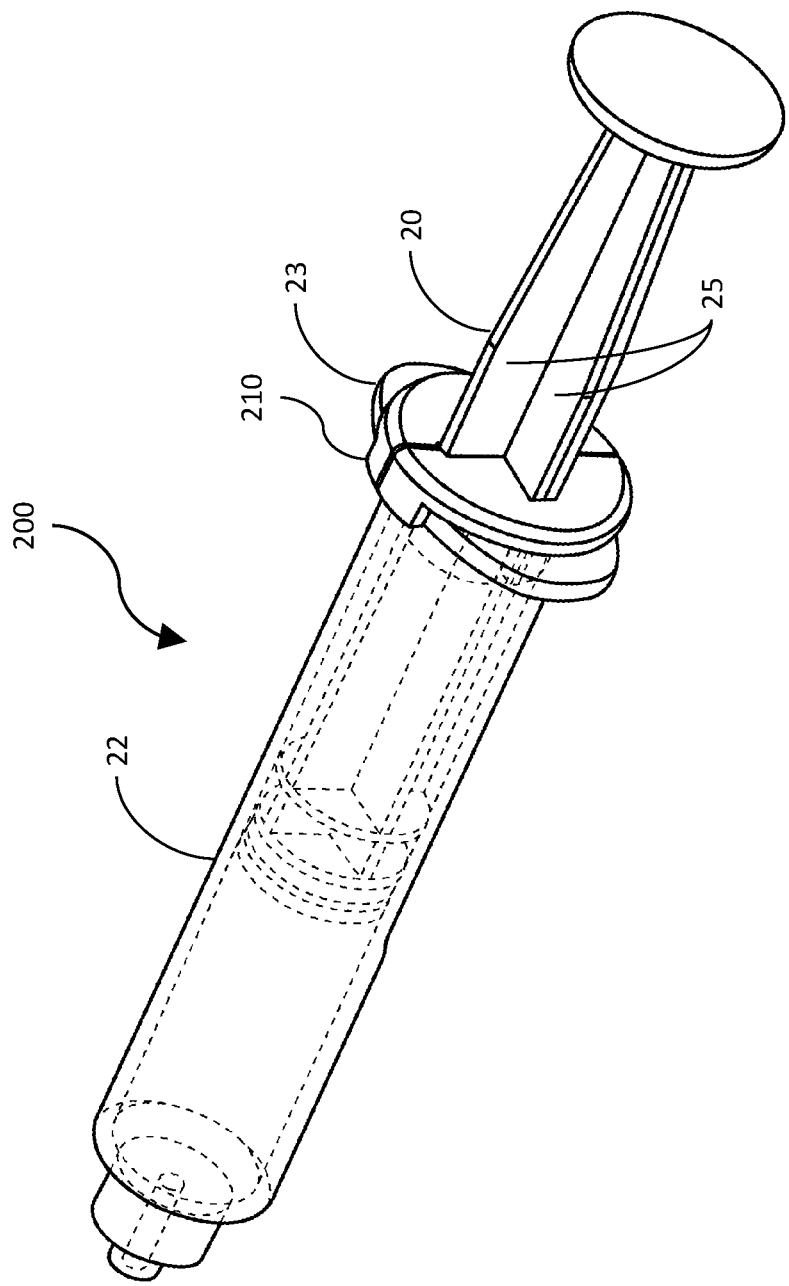

FIGS. 2A-2B illustrate an exemplary syringe 200 with a clip 210 that inhibits forward movement of a plunger 20. In some implementations, clip 210 can be a unitary, two-piece, three-piece, or more-piece clip structure configured to attach to barrel 22 to inhibit forward movement of the plunger when the clip engages the barrel.

In some implementations, the clip can be attachable to a portion of a standard syringe body, for example, to barrel flange 23, or within an open proximal end of the syringe barrel. As used herein, attaching to (or engaging) the barrel can include wrapping around as least a portion of the barrel.

The clip can also engage the plunger, for example, by wrapping around at least a portion of the plunger. Plunger 20 may include a number of longitudinal flanges 25 and the one or more clip pieces can include grooves 212 to receive the flanges 25, i.e., to clip onto and securely attach to one or more of the flanges.

In one implementation, the clip can be clipped onto the plunger (and the barrel) after withdrawing the plunger to remove fluid and can then inhibit the plunger from moving forward because the clip securely engages the plunger (e.g., by a tight friction fit).

The clip may also facilitate locking the plunger at a predetermined location after the plunger is pulled back to extract a particular volume of fluid, as described further below.

Figure 2C:
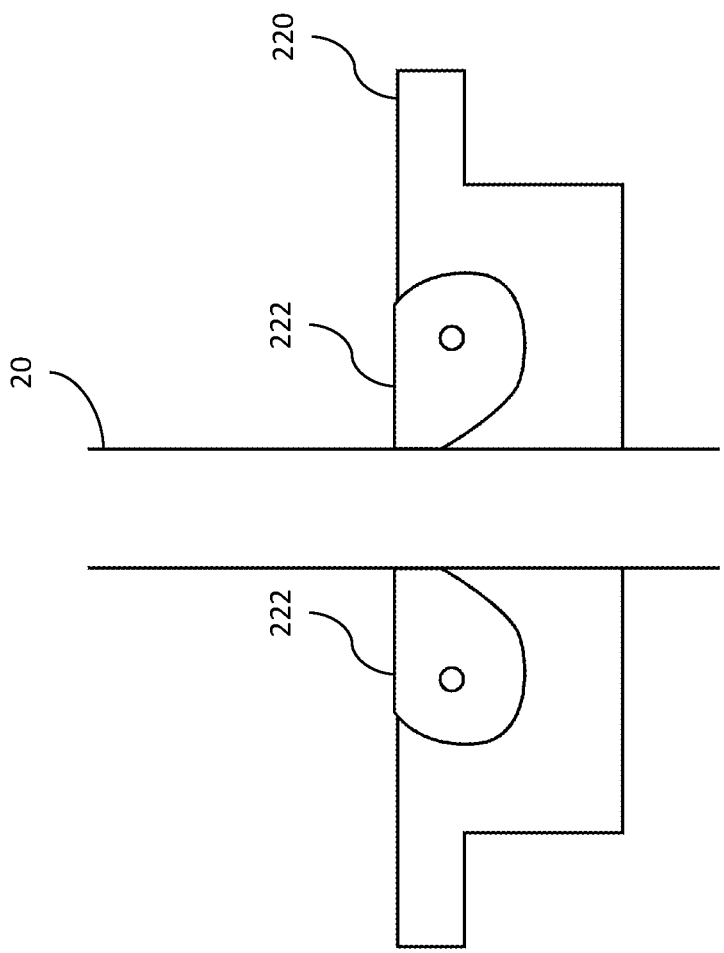
FIG. 2C illustrates an exemplary clip that includes cam locks in accordance with certain aspects of the present disclosure.

In an alternative implementation, as shown in FIG. 2C, a clip 220 can include one or more cam locks 222, which can allow movement of the plunger in one direction (e.g., backward, away from the syringe's distal end opening) and yet inhibit forward movement of the plunger.

Figure 3A:
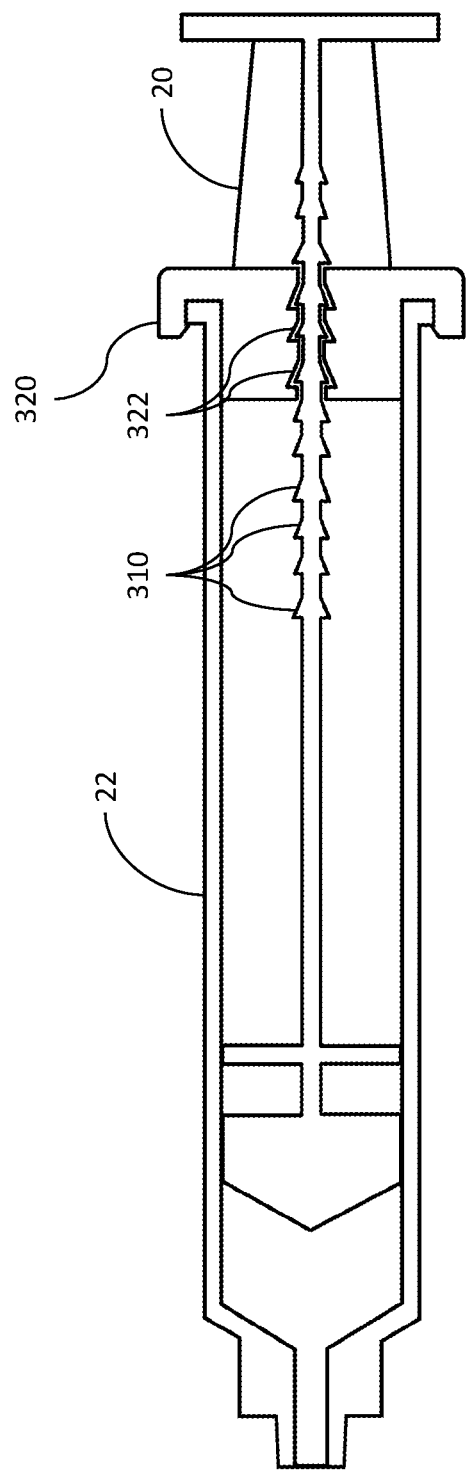
FIG. 3A illustrates an exemplary syringe including barbs on a plunger that engage with mating pockets on a clip in accordance with certain aspects of the present disclosure.
Figure 4A:
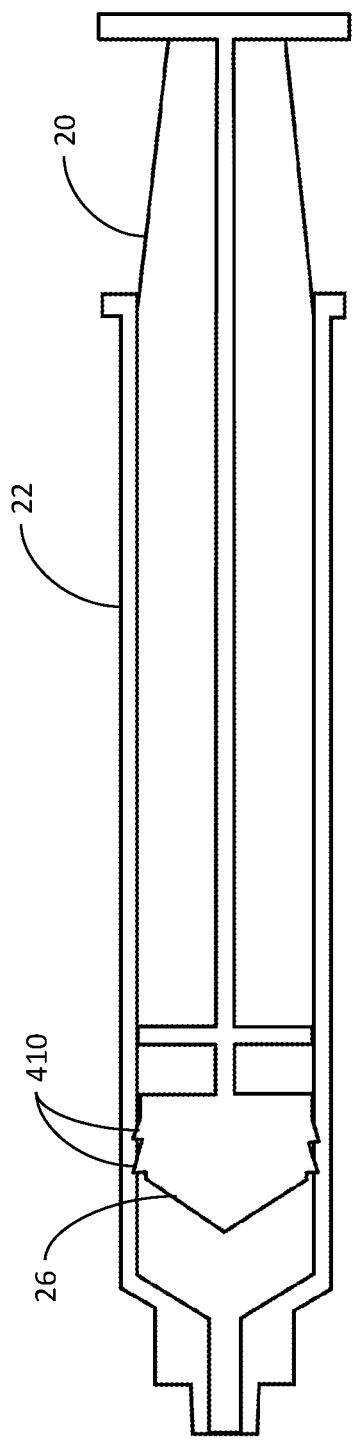
FIGS. 4A-4C illustrate exemplary implementations of a syringe where the plunger seal includes barbs or ribs in accordance with certain aspects of the present disclosure.

FIG. 3A illustrates an exemplary implementation including one or more barbs 310 on the plunger 20 that engage with mating pockets 322 on clip 320 to inhibit forward movement of the plunger. This allows the plunger to pull back away from the distal end of the barrel to variable positions to collect variable volumes of liquid, but also prevents forward motion of the plunger that may expel the collected liquid. In one implementation, the barbs can be integrated into a flange or flanges (e.g., flange 25 in FIG. 1). In other implementations, the barbs can be formed on an additional feature added to the plunger. In one design, the barbs can be spaced apart in increments that correspond to indicia provided on the outside of the barrel indicating or representing an amount or volume of fluid collected in the barrel. Barbs can also be utilized without mating pockets, for example, by simply interacting with the inside of the barrel, or another portion of the syringe, as shown by the example of FIG. 4A. Barbs may be sharp or have rounded features, and can be comprised of multiple materials (as shown in the example of FIG. 4C). As used herein, "barb(s)" are understood to refer to structure(s) that have a shape and/or constitution that will allow them to preferentially allow backward plunger movement but inhibit forward plunger movement. In some cases, barb(s) may merely resist, rather than completely inhibit, movement in the non-preferential direction. While the implementation of FIG. 3A illustrates barbs on the plunger, in other implementations, the mating pockets can be integrated into the plunger and the barbs can be integrated into the barrel.

Figure 3B:
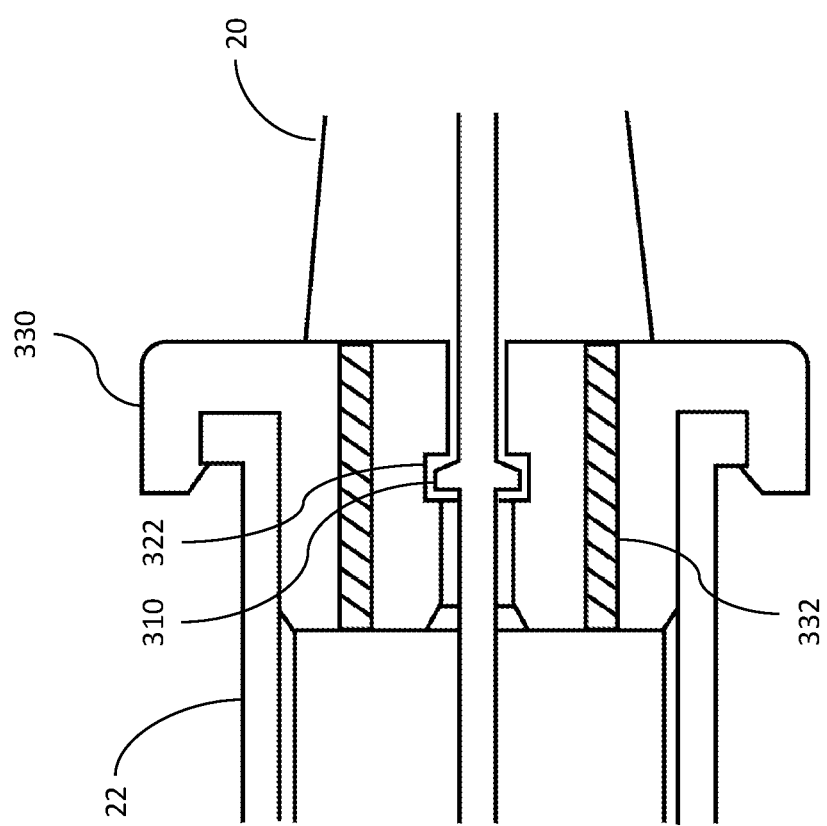
FIG. 3B illustrates an exemplary syringe including a single barb on a plunger that engages with a single mating pocket on a clip in accordance with certain aspects of the present disclosure.

FIG. 3B shows an exemplary implementation where a barb and a mating pocket are arranged to enable a particular draw volume. The FIG. 3B example utilizes a single barb 310 on plunger 20 and a single mating pocket 322 in the clip 330 but in other implementations, there can be multiple barbs and/or mating pockets. For example, there could be multiple barbs at the same position along the plunger, but on multiple flanges. The clip 330 can also incorporate spring elements 332 to compress the clip 330 against the plunger to improve performance.

Figure 3C:
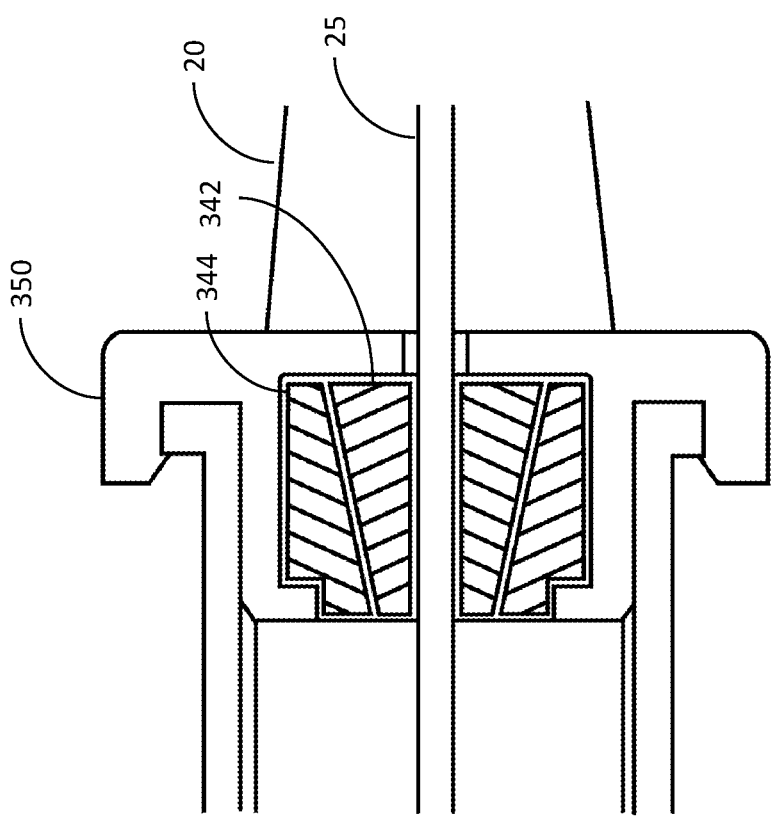
FIG. 3C illustrates an exemplary syringe including a wedge mechanism that resists forward movement of a plunger in accordance with certain aspects of the present disclosure.

FIG. 3C shows an exemplary implementation of a wedge mechanism that resists forward movement of the plunger. Clip 350 can include wedge mechanism 340 that includes an inner wedge 342 adjacent the plunger 20 (e.g., at flange 25) and an outer wedge 344 adjacent the barrel 22. The inner wedge 342 and the outer wedge 344 can be configured to provide frictional engagement of the inner wedge and the plunger in response to forward movement of the plunger. When the plunger is pushed to the left in FIG. 3C, the wedges squeeze the plunger (e.g., inner wedge 342 is frictionally pushed by flange 25 against outer wedge 344), which makes the plunger more difficult to move. In contrast, when plunger 20 moves to the right in FIG. 3C, the wedges open (e.g., inner wedge 342 pulls back and away from outer wedge 344) to reduce the friction between the plunger and the inner wedge. The plunger may have a rough surface, either with extending flexible members or circumscribing ridges, to increase friction with the wedge mechanism. The wedge mechanism can be made of a hard plastic or an elastomer to increase friction.

When the present disclosure refers to "clip(s)," the term is intended to refer to implementations where the clip is a separate piece or pieces that can be affixed to a syringe (e.g., as shown in FIG. 2A), but also implementations where the forward-movement restriction features described herein are directly integrated within a syringe body. As one example, the proximal end of the barrel itself can be configured to include mating pockets (similar to the implementation of FIG. 3A). In other words, the clip(s) described herein need not be removable. In the same vein, when the present disclosure refers to elements (e.g., mating pockets) being integrated into the barrel, this terminology is intended to cover implementations where the mating pockets are directly integrated into the syringe barrel and also implementations where the mating pockets are in a clip that is initially separate and then attached to the barrel.

Figure 4B:
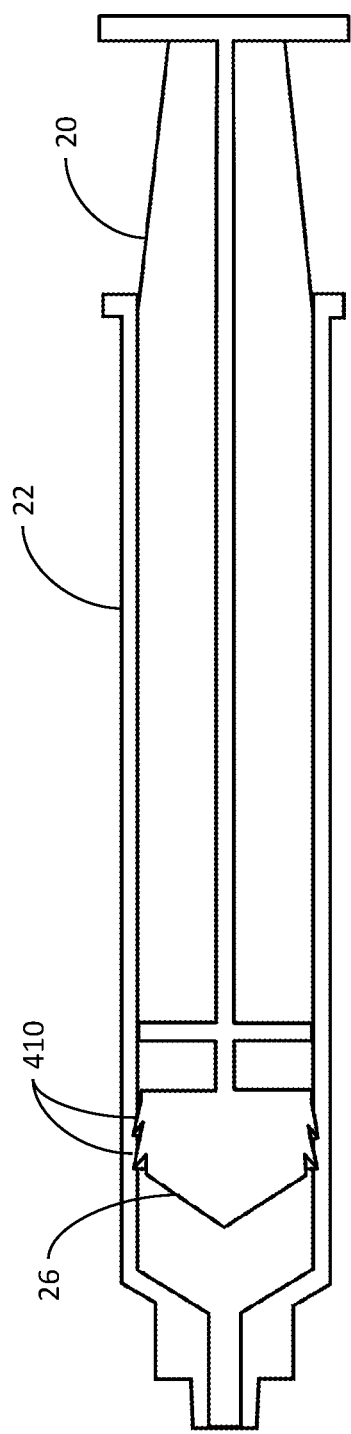
Figure 4C:
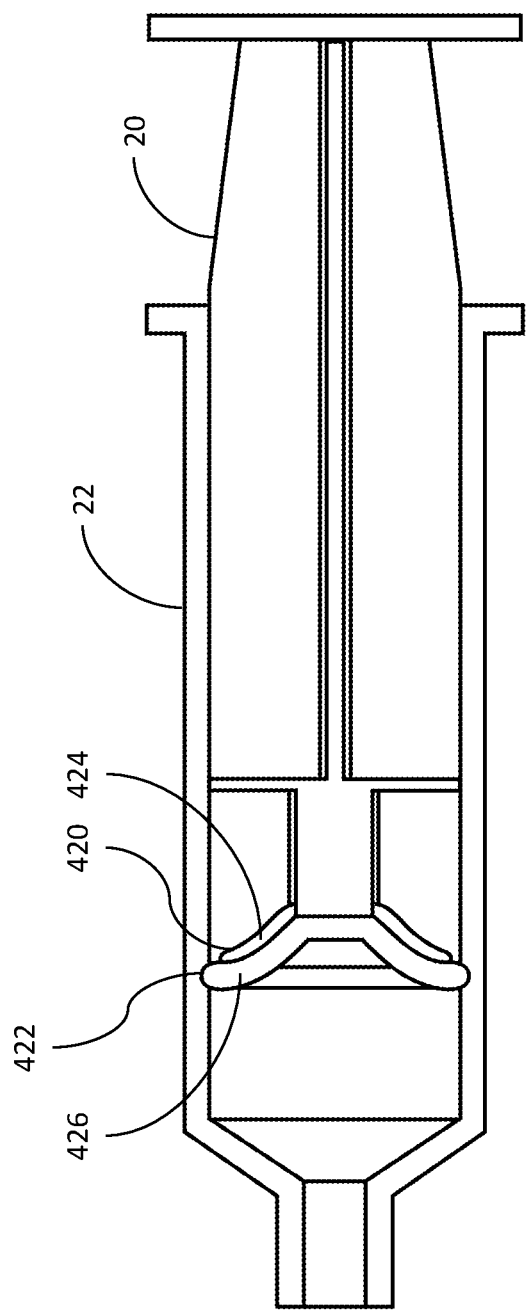

FIGS. 4A and 4B illustrate exemplary implementations where a plunger seal 26 uses or includes barbs 410 or ribs molded into the plunger seal on plunger 20 that engage barrel 22 and inhibit forward movement of the plunger 20. The barbs 410 in FIG. 4A are depicted as having a ramp (which can provide minimal resistance to backward motion of the plunger) and a vertical wall (that can inhibit forward motion of the plunger). The barbs 410 in FIG. 4B are similar but, instead of a vertical wall, they have another sloped surface, making the barbs 410 generally thinner than those shown in FIG. 4A. Utilizing different thicknesses for the barbs can vary their flexibility and thereby provide different amounts of resistance to forward movement of the plunger.

Barbs may be rounded and may also be comprised of multiple materials. FIG. 4C depicts an exemplary implementation where the plunger 20 includes barbs 420 having a more rounded tip 422 that engages the inside of the barrel 22. In addition, the implementation of FIG. 4C depicts barbs 420 that include multiple materials. For example, the barbs can include a rigid support 424 behind a portion of a more flexible member 426 that can form a better seal against the barrel. While certain implementations described herein depict barbs located on or near the plunger seal, it is contemplated that barbs could similarly be located on more proximal portions of the plunger (for example, on an edge or edges of the plunger flanges).

Figure 4D:
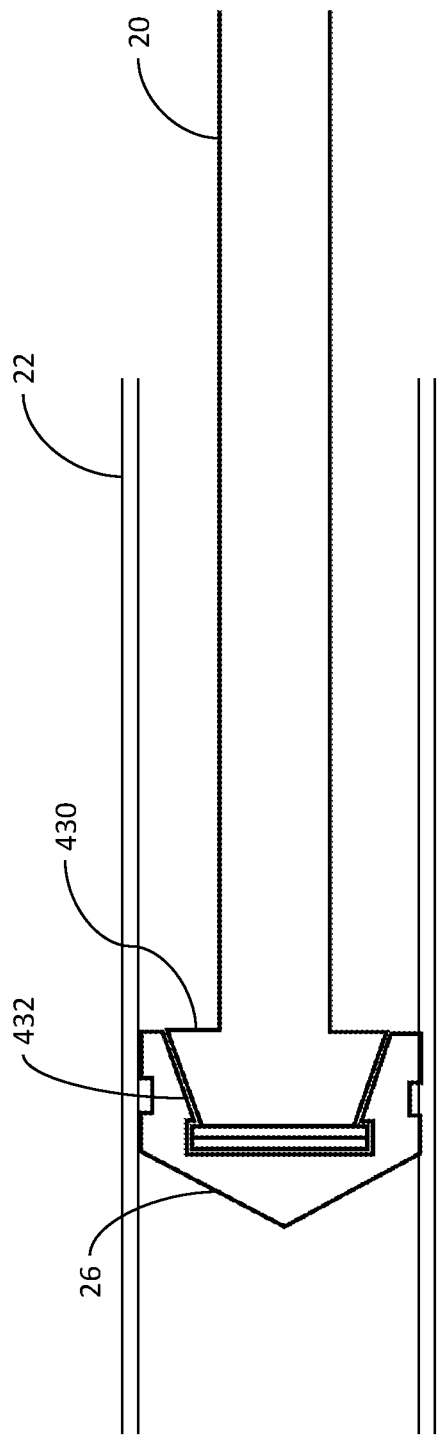
FIG. 4D illustrates an exemplary syringe including a wedge mechanism incorporated into the plunger seal in accordance with certain aspects of the present disclosure.

FIG. 4D shows an exemplary implementation of a plunger 20 including a plunger seal 26 and a wedge 430 at least partially inside the plunger seal 26 that is configured to inhibit forward movement of the plunger by increasing friction between the plunger seal 26 and the barrel 22. FIG. 4D shows wedge 430 on the plunger and a mating shape 432 formed in the plunger seal 26. When the plunger 20 is pulled to the right (to fill the syringe with fluid), the plunger acts normally. When pushed to the left (to expel fluid), the wedge pushes against the mating shape 432 to expand the plunger seal 26 and increase friction against the inner walls of the barrel 22, making it more difficult to advance and therefore inhibiting forward movement of the plunger 20 relative to the barrel 22.

Figure 5:
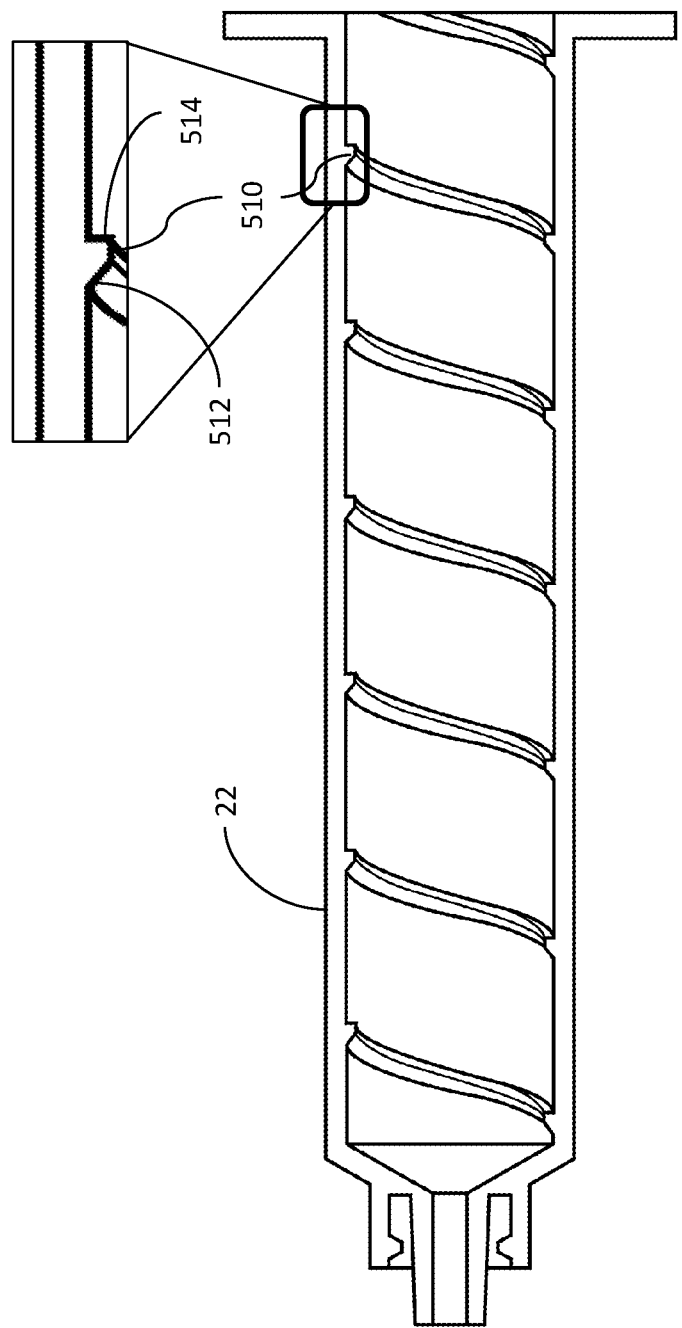
FIG. 5 illustrates an exemplary syringe with internal ridges on the barrel in accordance with certain aspects of the present disclosure.

FIG. 5 illustrates an exemplary implementation where barrel 22 has an inner ridge 510 having a ramp 512 that inclines as it progresses towards the proximal end of the barrel and then transitions to a vertical wall 514. Ramp 512 can permit backward movement of a plunger over itself, and vertical wall 514 can inhibit forward movement of the plunger (for example, by engaging against a plunger seal).

In some implementations, inner ridge 510 can be formed using a thread molded on the internal diameter of the barrel 22 and can have a helical design, as shown in FIG. 5. For such a helical design, the plunger seal will continually engage the inner ridge, resulting in a constant frictional resistance to forward movement. In other implementations, an inner ridge can be located at one place inside the circumference of the barrel (e.g., a circular inner ridge around the barrel near the proximal end). In such implementations, forward movement can be inhibited when the seal moves past the ridge.

Figure 6B:
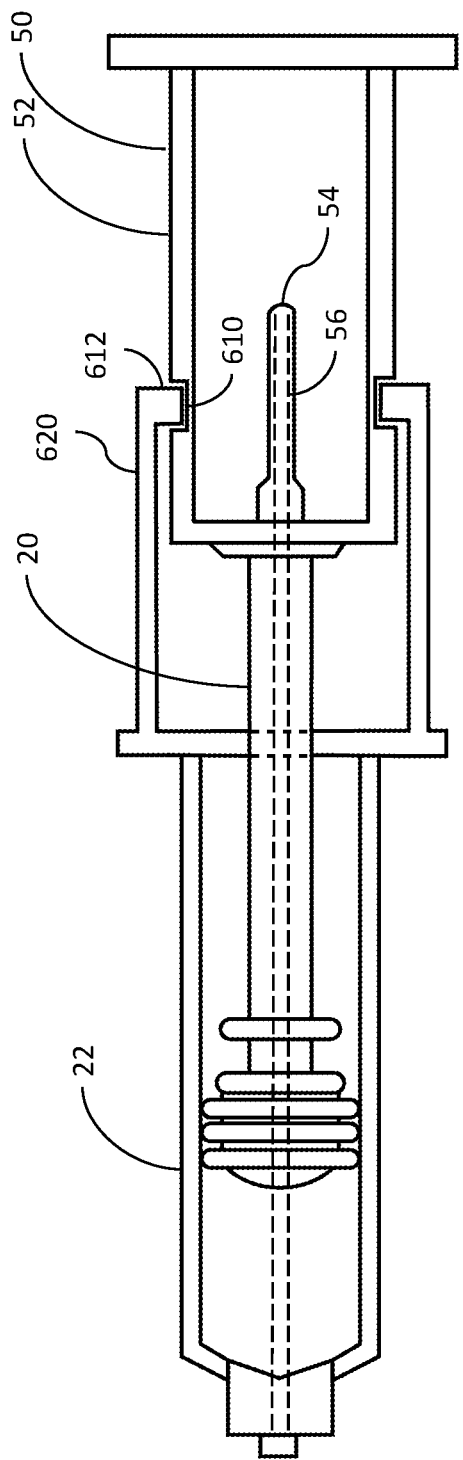

In some implementations, the proximal end of plunger 20 can include a fluid collection device similar to those used in a Vacutainer™ system. More generally, an interface 50 on the proximal end of the plunger can have an open-ended cylinder 52 with a collection needle 54 that includes a sampling channel 56 through the length of plunger 20 to an opening at a proximal end of the plunger. The present disclosure contemplates a syringe that can include, as shown in FIGS. 6A and 6B, the use of mating pockets 610 on the interface 50 that engage with barb(s) 612 extending from the collection adaptor 620 portion of the barrel 22, to inhibit forward movement of the plunger 20. In other implementations, the configuration of the barbs/mating pockets can be reversed with the interface including barbs configured to engage mating pockets on the collection adapter 620 to inhibit forward movement of the plunger 20.

The barbs 612 can include, for example, a ramp and a vertical wall (as shown in FIG. 6A) or an inwardly-directed tab (as shown in FIG. 6B) and can interface with corresponding mating pockets 610. The barb(s) can be configured to allow for a user-selected volume or a predetermined volume, similar to other implementations described herein.

Figure 7A:
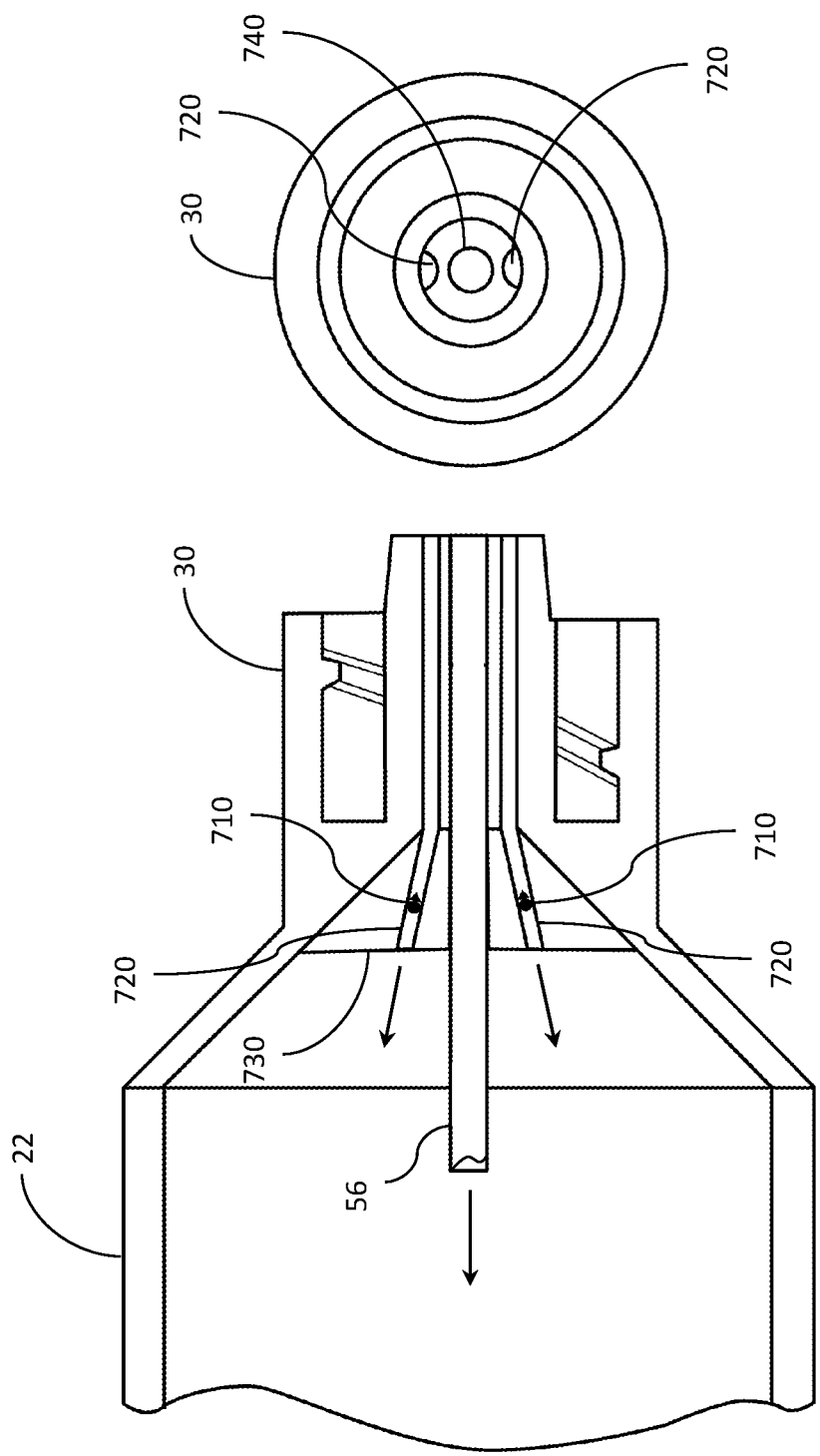
FIGS. 7A-C illustrate exemplary implementations of syringe tips having various types of check valves in accordance with certain aspects of the present disclosure.
Figure 7B:
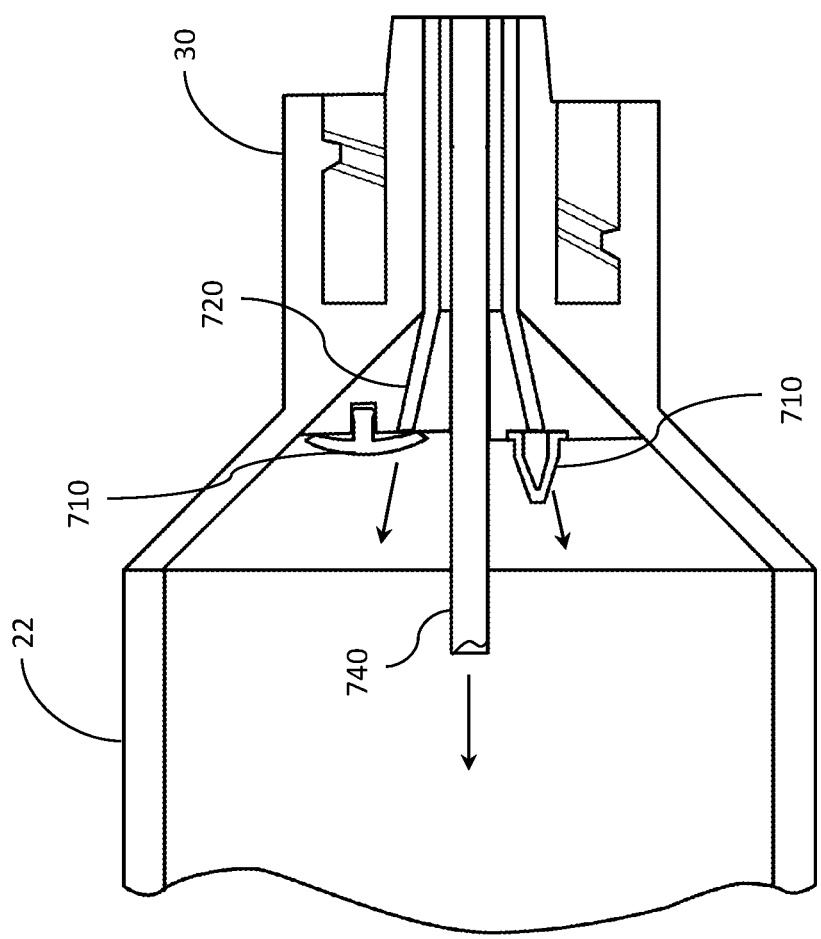
Figure 7C:
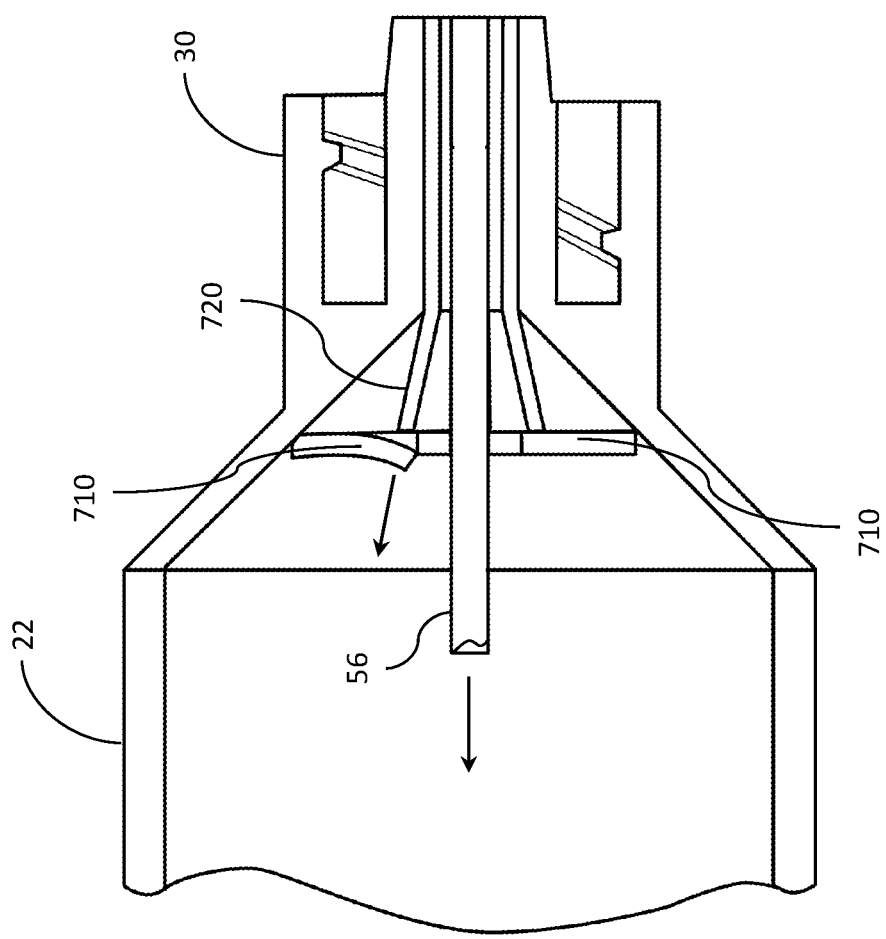

FIGS. 7A, 7B, and 7C show exemplary implementations of syringe tips including check valves. In some implementations, a wedge-shaped member 730 in the tip can allow for additional room to incorporate check valve(s). FIG. 7A depicts a sampling channel 56 from the tip of the syringe, through the plunger (see also, FIG. 6A), to an interface 50 having an open-ended cylinder with a collection needle 54. The tip can also include a barrel channel 720 from the end of the syringe into barrel 22. A check valve 710 can be placed in fluid communication with the barrel channel 720, the check valve 710 configured to check forward expulsion of fluids from the barrel. In operation, check-valve 710 can allow an initial portion of liquid (which may be contaminated) to enter the barrel, but prevent that liquid from being pushed back out of the syringe. Later portions of liquid can then be drawn through sampling channel 56.

The check valve can be a ball valve (FIG. 7A), umbrella or duck-bill valve (FIG. 7B), flapper valve (FIG. 7C, showing one open and one closed), or any other type of one-way fluid valve.

Figure 7D:
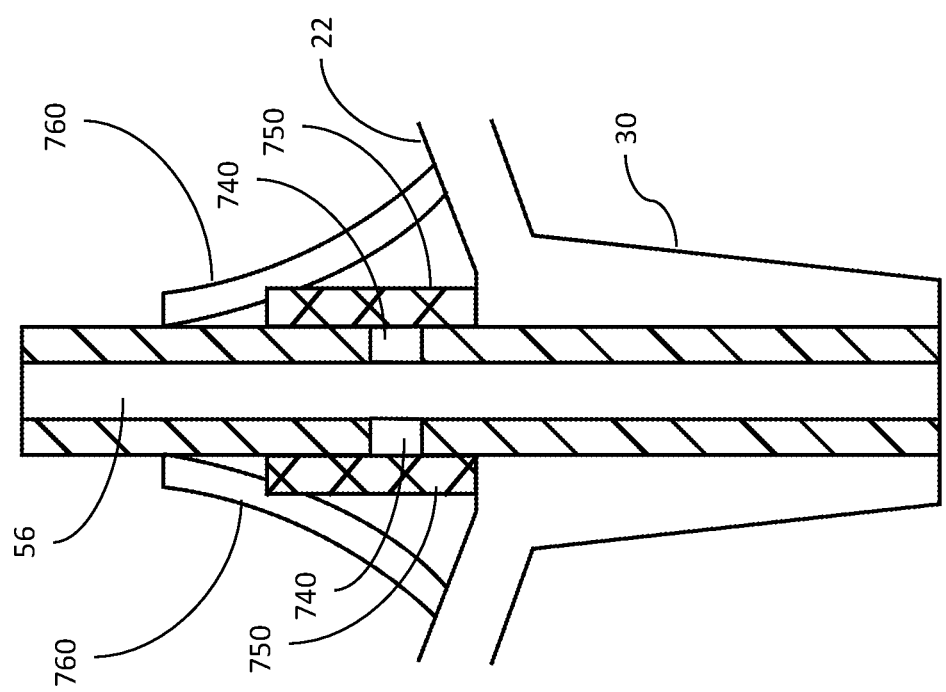
FIG. 7D illustrates an exemplary syringe tip design having barrel channel(s) off of a sampling channel and the use of check valves in accordance with certain aspects of the present disclosure.

FIG. 7D shows an exemplary a sampling channel with barrel channels covered by two implementations of check valves. As shown in FIG. 7D, (similar to FIG. 7A and again with some elements shown in FIG. 6B) the system can include a sampling channel 56 from a tip of the syringe, through the plunger, to an interface 50 having an open-ended cylinder with a collection needle 54. There can be one or more barrel channels 740 from the sampling channel 56 into the barrel 22. A check valve (e.g., 750 or 760) can be in communication with the barrel channel, with the check valve configured to check forward expulsion of fluids from the barrel 22. FIG. 7D shows two types of check valves, which may be present in respective implementations. In one implementation, a tubing check valve 750 can be formed as an annular segment of flexible material that covers barrel channels 740. When the plunger is pulled back and a vacuum forms in barrel 22, the vacuum can pull the flexible material away from the sampling channel to allow fluid to enter barrel 22. In another implementation, duck-bill valve(s) 760 can be utilized to cover the barrel channel(s) 740. The duckbill valves(s) 760 can then similarly open when a vacuum is present in barrel 22. In some implementations, such check valves can be attached to, or placed on external attachments rather than directly on sampling channel 56.

Figure 8A:
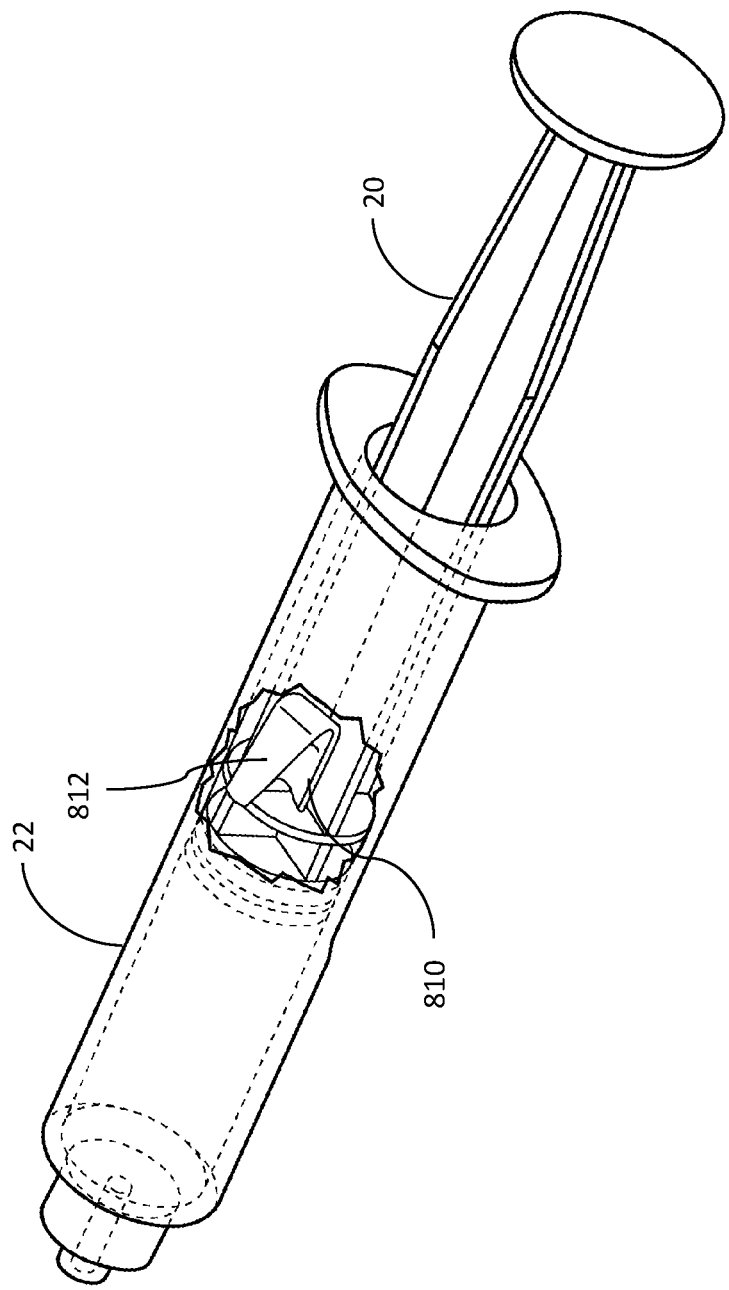
FIGS. 8A and 8B illustrate an exemplary implementation of a syringe using a spring clip to inhibit forward movement of the plunger in accordance with certain aspects of the present disclosure.
Figure 8B:
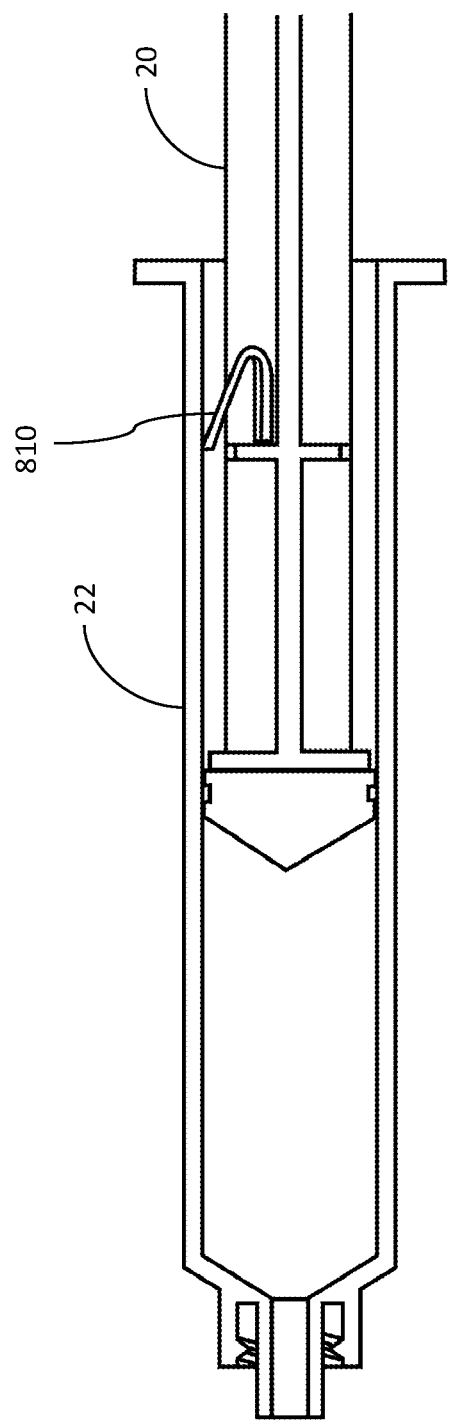

FIGS. 8A and 8B illustrate exemplary implementations using a spring clip 810 contacting the barrel 22 of the syringe to inhibit forward movement of the plunger 20. The spring clip can be made of spring steel and can be pre-loaded against the inside wall of the syringe body. When the plunger is pulled back, the spring clip can slide along the inside walls of the barrel. When pushed forward, the spring force in the spring clip will press its laterally extending arm 812 outward to dig into the wall of the barrel and inhibit forward movement of the plunger.

Figure 9A:
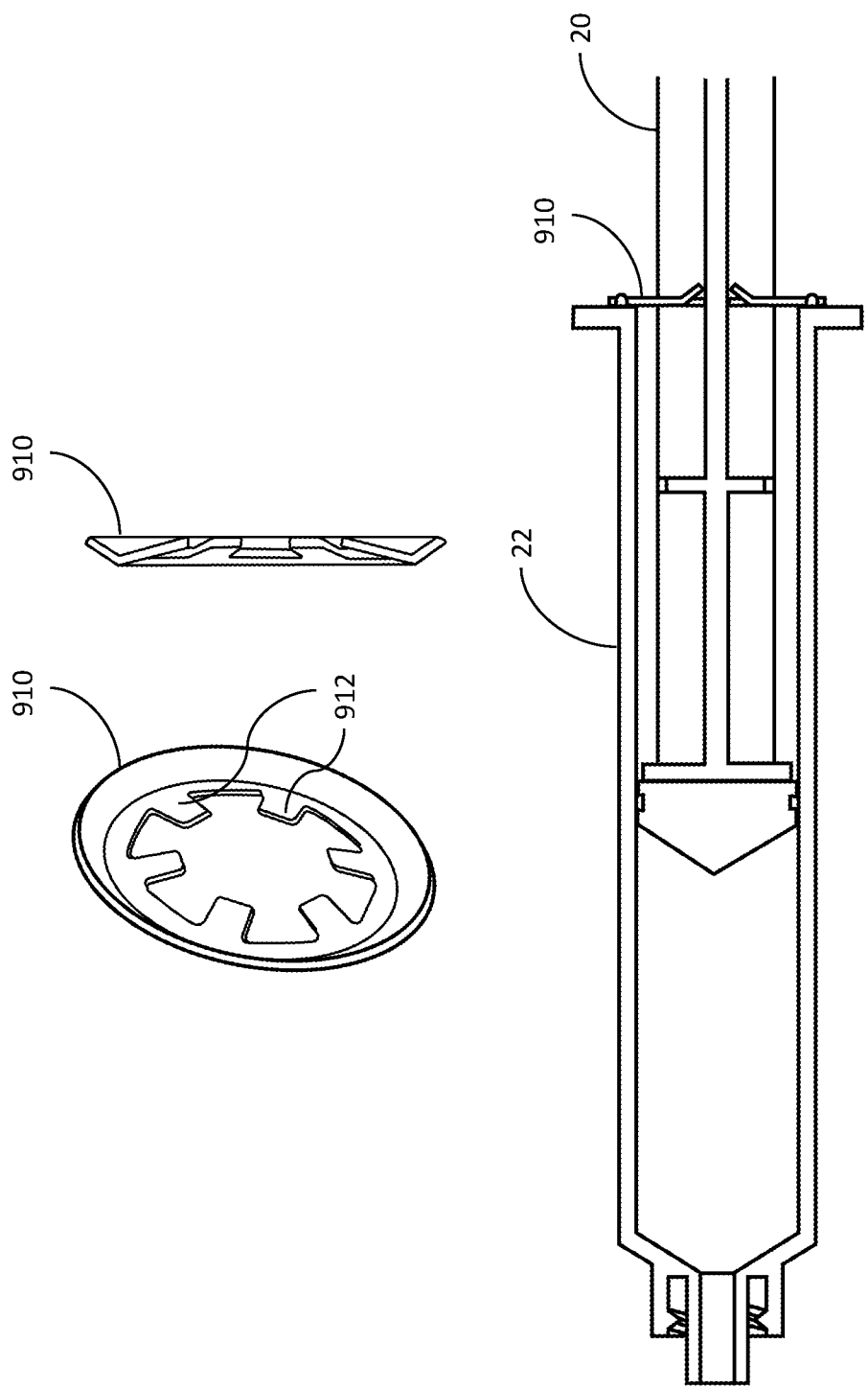
FIGS. 9A and 9B illustrate exemplary implementations of a syringe using a ring clip to inhibit forward movement of the plunger in accordance with certain aspects of the present disclosure.
Figure 9B:
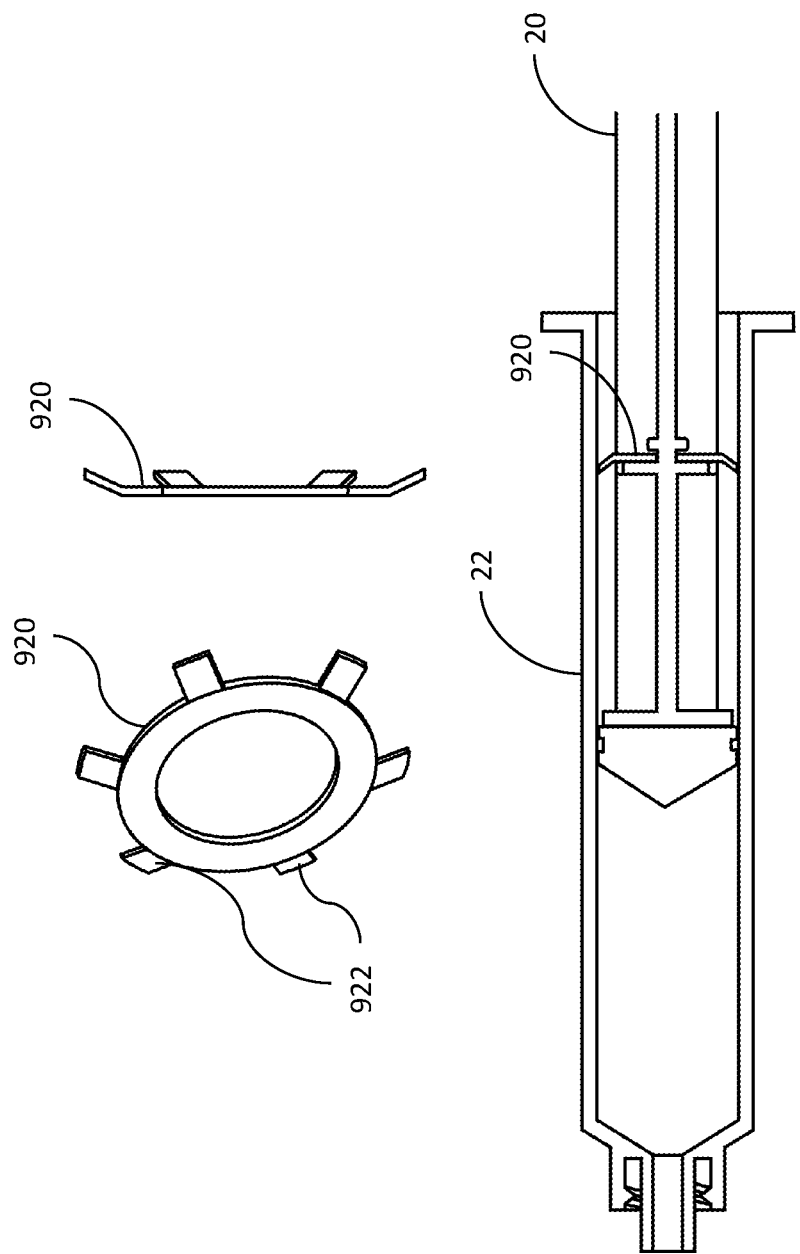

FIGS. 9A and 9B illustrate exemplary implementations using a ring clip to inhibit forward movement of the plunger. Perspective and side views of the ring clip are shown above the sectional views. The ring clip can be a one-way clip-on ring that can clip on plunger 20 or over a proximal opening of barrel 22. FIG. 9A shows plunger 20 including an internal ring clip 910 (i.e., with prongs 912 extending internally) configured to contact the barrel 22 of the syringe and to inhibit forward movement of the plunger 20. This can allow the plunger to move to the right (backward) in FIG. 9A and inhibit the plunger from moving to the left (forward). FIG. 9B shows barrel 22 including an external ring clip 920 (i.e., with prongs 922 extending externally) configured to contact plunger 20 and to inhibit forward movement of the plunger.

Figure 10:
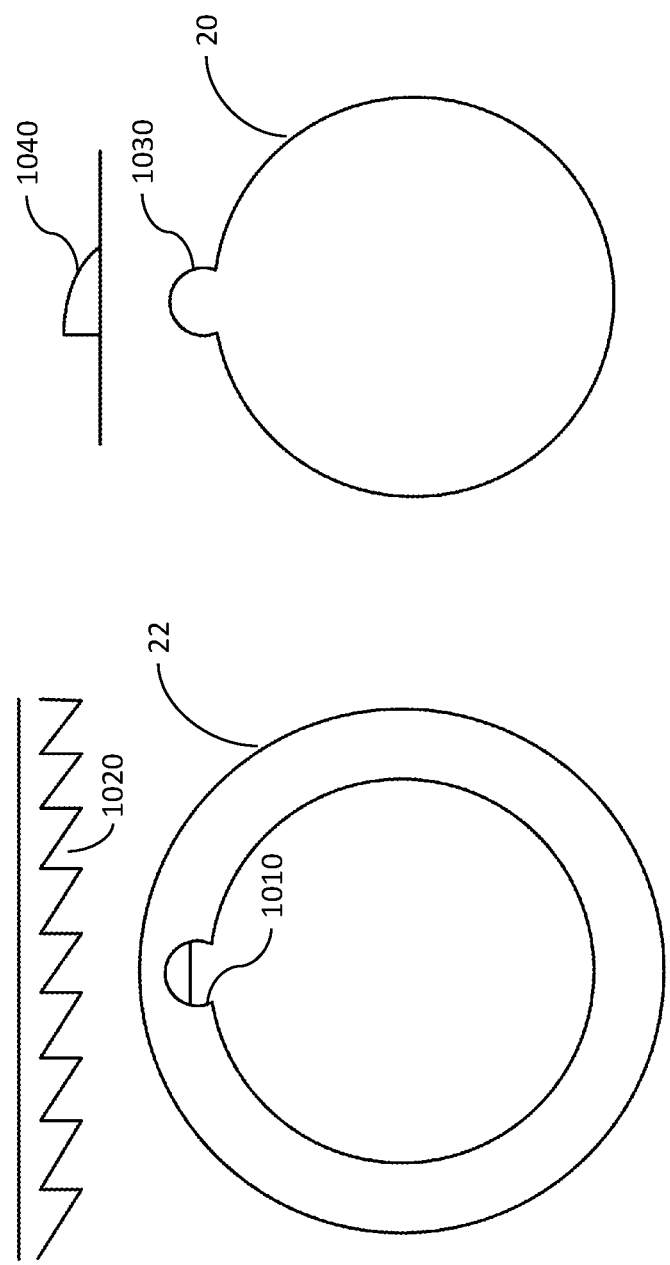
FIG. 10 illustrates an exemplary syringe design with the barrel having a groove and the plunger having a protrusion that mates with the groove in accordance with certain aspects of the present disclosure.

FIG. 10 illustrates an exemplary implementation where an internal surface of barrel 22 includes a groove 1010 having mating pocket(s) 1020 and where plunger 20 includes a protrusion 1030 including barb(s) 1040 configured to inhibit forward movement of the plunger 20. The interaction of the plunger protrusion having barbs with the groove in the barrel can both prevent rotation of plunger 20 relative to barrel 22 and also inhibit forward movement of the plunger.

The present disclosure contemplates that other ratcheting-type mechanisms can be implemented to provide the preferential movement described herein. For example, a mechanism in the form of multiple steps, grooves, ramps, or the like, can be formed on the inner portion of the barrel, or on the plunger inside the barrel where the ratchets engage with the exterior of the barrel. The disclosed mechanisms can include annular rings, segmented sections, or protrusions at various points along the plunger either in a linear fashion, spiraling, or stair-stepped. In still other implementations, ramps or bumps can be provided on outside of the barrel to interact with an external surface of the plunger that overlays the outside of the barrel.

In the following, further features, characteristics, and exemplary technical solutions of the present disclosure will be described in terms of items that may be optionally claimed in any combination:

Item 1: A system comprising: a syringe comprising: a barrel configured to hold a fluid; and a plunger configured to draw the fluid into the barrel when the plunger is pulled backward through the barrel, the syringe being configured to inhibit forward movement of the plunger.

Item 2: The system of Item 1, further comprising one or more mating pockets configured to engage one or more barbs to inhibit forward movement of the plunger.

Item 3: The system of any one of the preceding Items, wherein the one or more mating pockets are integrated into the barrel and the one or more barbs are integrated into the plunger.

Item 4: The system of any one of the preceding Items, wherein the one or more mating pockets are integrated into the plunger and the one or more barbs are integrated into the barrel.

Item 5: The system of any one of the preceding Items, wherein the one or more mating pockets are integrated into a clip configured to be removably attached at least partially around the plunger.

Item 6: The system of any one of the preceding Items, wherein the one or more barbs and the one or more mating pockets are arranged to enable a predetermined draw volume.

Item 7: The system of any one of the preceding Items, wherein the plunger includes an interface having an open-ended cylinder with a collection needle and a sampling channel through the plunger.

Item 8: The system of any one of the preceding Items, wherein the interface includes one or more mating pockets configured to engage one or more barbs to inhibit forward movement of the plunger.

Item 9: The system of any one of the preceding Items, wherein the interface includes one or more barbs configured to engage one or more mating pockets to inhibit forward movement of the plunger.

Item 10: The system of any one of the preceding Items, wherein the plunger includes a plunger seal having one or more barbs, the one or more barbs configured to inhibit forward movement of the plunger.

Item 11: The system of any one of the preceding Items, wherein the barrel includes a groove having one or more mating pockets and the plunger includes a protrusion having one or more barbs configured to inhibit forward movement of the plunger.

Item 12: The system of any one of the preceding Items, the system further comprising: a clip configured to attach to the barrel and to securely attach to the plunger and inhibit forward movement of the plunger when the clip engages the barrel.

Item 13: The system of any one of the preceding Items, the system further comprising an inner wedge adjacent the plunger and an outer wedge adjacent the barrel wherein the inner wedge and outer wedge are configured to provide frictional engagement of the inner wedge and the plunger in response to forward movement of the plunger.

Item 14: The system of any one of the preceding Items, wherein the plunger includes one or more spring clips configured to contact the barrel of the syringe and to inhibit forward movement of the plunger.

Item 15: The system of any one of the preceding Items, wherein the plunger includes one or more internal ring clips configured to contact the barrel of the syringe and to inhibit forward movement of the plunger.

Item 16: The system of any one of the preceding Items, wherein the barrel includes one or more external ring clips configured to contact the plunger and to inhibit forward movement of the plunger.

Item 17: The system of any one of the preceding Items, the system further comprising one or more cam locks configured to inhibit forward movement of the plunger.

Item 18: The system of any one of the preceding Items, wherein the barrel includes an inner ridge, the inner ridge having a ramp that inclines towards the proximal end to a vertical wall, the ramp permitting backward movement of the plunger over the ramp and the vertical wall inhibiting forward movement of the plunger.

Item 19: The system of any one of the preceding Items, the plunger further comprising: a plunger seal; and a wedge at least partially inside the plunger seal and configured to inhibit forward movement of the plunger by increasing friction between the plunger seal and the barrel.

Item 20: The system of any one of the preceding Items, the system further comprising: a sampling channel from a tip of the syringe, through the plunger, to an interface having an open-ended cylinder with a collection needle; a barrel channel from the tip of the syringe into the barrel; and a check valve in communication with the barrel channel, the check valve configured to check forward expulsion of fluids from the barrel.

Item 21: The system of any one of the preceding Items, the system further comprising: a sampling channel from a tip of the syringe, through the plunger, to an interface having an open-ended cylinder with a collection needle; a barrel channel from the sampling channel into the barrel; and a check valve in communication with the barrel channel, the check valve configured to check forward expulsion of fluids from the barrel.

Item 22: A method comprising utilization of the system of any one of the preceding Items.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. The implementations described above can be directed to various combinations and subcombinations of the disclosed features and/or combinations and subcombinations of further features noted above. Furthermore, above described advantages are not intended to limit the application of any issued claims to processes and structures accomplishing any or all of the advantages.

Additionally, section headings shall not limit or characterize the invention(s) set out in any claims that may issue from this disclosure. Further, the description of a technology in the "Background" is not to be construed as an admission that technology is prior art to any invention(s) in this disclosure. Neither is the "Summary" to be considered as a characterization of the invention(s) set forth in issued claims. Multiple inventions may be set forth according to the elements of the multiple claims issuing from this disclosure, and such claims accordingly define the invention(s), and their equivalents, that are protected thereby.

What is claimed is:

1. A system comprising:
  a syringe comprising:
    a barrel configured to hold a fluid;
    a plunger configured to draw the fluid into the barrel when the plunger is pulled backward through the barrel; and
    one or more internal features comprising:
      at least one inner ridge on the barrel;
      wherein the syringe is configured such that the at least one inner ridge engages the plunger and causes frictional resistance to forward movement when the plunger moves past the at least one inner ridge, and
      wherein the one or more internal features are spaced apart in increments that correspond to indicia provided on an outside of the barrel indicating an amount of fluid collected in the barrel.

2. The system of claim 1, wherein the one or more internal features are arranged to enable a predetermined draw volume.

3. The system of claim 1, wherein the one or more internal features includes a plurality of internal features.

4. The system of claim 3, wherein the plurality of internal features is spaced apart longitudinally in increments.

5. The system of claim 4, wherein each increment corresponds to a specific incremental volume within the barrel.

6. The system of claim 1, further configured such that forward movement of the plunger is frictionally resisted when a plunger seal moves past the one or more internal features.

7. The system of claim 1, wherein an inner ridge is arranged to enable a predetermined draw volume.

8. The system of claim 1, further configured such that forward movement of the plunger is frictionally resisted when a plunger seal moves past one of the at least one inner ridge(s) on the barrel.

9. The system of claim 1, further comprising an inner ridge having a ramp that inclines towards a proximal end of the barrel to a vertical wall, the ramp permitting backward movement of the plunger over the ramp.

10. The system of claim 1, wherein the one or more internal features comprise the barrel having inner ridges spaced apart in increments that correspond to indicia provided on an outside of the barrel indicating an amount of fluid collected in the barrel.

11. The system of claim 1, wherein the one or more internal features further comprise at least one mating pocket configured to engage one of the at least one inner ridge(s) on the barrel.

12. The system of claim 1, wherein the plunger includes an interface having an open-ended cylinder with a collection needle and a sampling channel through the plunger.

13. The system of claim 1, wherein the at least one inner ridge on the barrel comprises a circular inner ridge inside the circumference of the barrel.

14. The system of claim 1, wherein there is one inner ridge on the barrel, located near a proximal end of the barrel.

15. The system of claim 1, wherein there is one inner ridge on the barrel that is a circular inner ridge, located near a proximal end of the barrel.

16. A system comprising:
   a syringe comprising:
      a barrel configured to hold a fluid;
      a plunger configured to draw the fluid into the barrel when the plunger is pulled backward through the barrel; and
      a plurality of internal features spaced apart longitudinally in increments, the plurality of internal features comprising:
         at least one inner ridge on the barrel;
         wherein the syringe is configured such that the at least one inner ridge engages the plunger and causes frictional resistance to forward movement when the plunger moves past the at least one inner ridge.

17. The system of claim 16, wherein each increment corresponds to a specific incremental volume within the barrel.

18. The system of claim 16, wherein the plurality of internal features are arranged to enable a predetermined draw volume.

19. The system of claim 16, wherein an inner ridge is arranged to enable a predetermined draw volume.

20. The system of claim 16, further comprising an inner ridge having a ramp that inclines towards a proximal end of the barrel to a vertical wall, the ramp permitting backward movement of the plunger over the ramp.

21. The system of claim 16, wherein the one or more internal features comprise the barrel having inner ridges spaced apart in increments that correspond to indicia provided on an outside of the barrel indicating an amount of fluid collected in the barrel.

22. The system of claim 16, wherein the one or more internal features further comprise at least one mating pocket configured to engage one of the at least one inner ridge(s) on the barrel.

23. The system of claim 16, wherein the plunger includes an interface having an open-ended cylinder with a collection needle and a sampling channel through the plunger.

24. The system of claim 16, wherein the at least one inner ridge on the barrel comprises a circular inner ridge inside the circumference of the barrel.

25. The system of claim 16, wherein there is one inner ridge on the barrel, located near a proximal end of the barrel.

26. The system of claim 16, wherein there is one inner ridge on the barrel that is a circular inner ridge, located near a proximal end of the barrel.

27. A system comprising:
   a syringe comprising:
      a barrel configured to hold a fluid;
      a plunger configured to draw the fluid into the barrel when the plunger is pulled backward through the barrel; and
      one or more internal features comprising:
         at least one inner ridge on the barrel;
         wherein the syringe is configured such that the at least one inner ridge engages the plunger and causes frictional resistance to forward movement when the plunger moves past the at least one inner ridge, and
         wherein the syringe is configured such that forward movement of the plunger is frictionally resisted when a plunger seal moves past the one or more internal features.

28. The system of claim 27, wherein each increment corresponds to a specific incremental volume within the barrel.

29. The system of claim 27, wherein the one or more internal features are arranged to enable a predetermined draw volume.

30. The system of claim 27, wherein an inner ridge is arranged to enable a predetermined draw volume.

31. The system of claim 27, further comprising an inner ridge having a ramp that inclines towards a proximal end of the barrel to a vertical wall, the ramp permitting backward movement of the plunger over the ramp.

32. The system of claim 27, wherein the one or more internal features comprise the barrel having inner ridges spaced apart in increments that correspond to indicia provided on an outside of the barrel indicating an amount of fluid collected in the barrel.

33. The system of claim 27, wherein the one or more internal features further comprise at least one mating pocket configured to engage one of the at least one inner ridge(s) on the barrel.

34. The system of claim 27, wherein the plunger includes an interface having an open-ended cylinder with a collection needle and a sampling channel through the plunger.

35. The system of claim 27, wherein the at least one inner ridge on the barrel comprises a circular inner ridge inside the circumference of the barrel.

36. The system of claim 27, wherein there is one inner ridge on the barrel, located near a proximal end of the barrel.

37. The system of claim 27, wherein there is one inner ridge on the barrel that is a circular inner ridge, located near a proximal end of the barrel.

38. A system comprising:
a syringe comprising:
   a barrel configured to hold a fluid;
   a plunger configured to draw the fluid into the barrel when the plunger is pulled backward through the barrel; and
   one or more internal features comprising:
      at least one inner ridge on the barrel;
      wherein the syringe is configured such that the at least one inner ridge engages the plunger and causes frictional resistance to forward movement when the plunger moves past the at least one inner ridge, and
      wherein the syringe is configured such that forward movement of the plunger is frictionally resisted when a plunger seal moves past one of the at least one inner ridge(s) on the barrel.

39. The system of claim 38, wherein each increment corresponds to a specific incremental volume within the barrel.

40. The system of claim 38, wherein the one or more internal features are arranged to enable a predetermined draw volume.

41. The system of claim 38, wherein an inner ridge is arranged to enable a predetermined draw volume.

42. The system of claim 38, further comprising an inner ridge having a ramp that inclines towards a proximal end of the barrel to a vertical wall, the ramp permitting backward movement of the plunger over the ramp.

43. The system of claim 38, wherein the one or more internal features comprise the barrel having inner ridges spaced apart in increments that correspond to indicia provided on an outside of the barrel indicating an amount of fluid collected in the barrel.

44. The system of claim 38, wherein the one or more internal features further comprise at least one mating pocket configured to engage one of the at least one inner ridge(s) on the barrel.

45. The system of claim 38, wherein the plunger includes an interface having an open-ended cylinder with a collection needle and a sampling channel through the plunger.

46. The system of claim 38, wherein the at least one inner ridge on the barrel comprises a circular inner ridge inside the circumference of the barrel.

47. The system of claim 38, wherein there is one inner ridge on the barrel, located near a proximal end of the barrel.

48. The system of claim 38, wherein there is one inner ridge on the barrel that is a circular inner ridge, located near a proximal end of the barrel.

* * * * *